United States Patent [19]

Robinson, III et al.

[11] Patent Number: 5,510,486
[45] Date of Patent: Apr. 23, 1996

[54] PROCESS FOR PREPARING 2-(1-AZABICYCLO[2.2.2]OCT-3-YL)-2,3,3A,4,5,6-HEXAHYDRO-1H-BENZ[DE]ISOQUINOLIN-1-ONE

[75] Inventors: James Robinson, III, East Palo Alto; John C. Rohloff, Mountain View; Bruce A. Kowalczyk, Cupertino, all of Calif.

[73] Assignee: Syntex (U.S.A.) Inc., Palo Alto, Calif.

[21] Appl. No.: 280,265

[22] Filed: Jul. 26, 1994

[51] Int. Cl.$^6$ .................................................. C07D 221/04
[52] U.S. Cl. .................................................. 546/99
[58] Field of Search ........................................ 546/99

[56] References Cited

U.S. PATENT DOCUMENTS 5,202,318  4/1993  Berger et al. ...................... 514/211
5,202,333  4/1993  Berger et al. ...................... 514/296

OTHER PUBLICATIONS

Morrison & Boyd "Organic Chemistry" 3rd Ed. p. 756.

*Primary Examiner*—Gary Geist
*Assistant Examiner*—Catherine Kilby Scalzo
*Attorney, Agent, or Firm*—Wayne W. Montgomery; Derek P. Freyberg

[57] ABSTRACT

This invention relates to a process for preparing 2-(1-azabicyclo[2.2.2]oct-3-yl)-2,3,3a,4,5,6-tetrahydro-1H-benz[de]isoquinolin-1-one, particularly 2-(1-azabicyclo[2.2.2]oct-3S-yl)-2,3,3aS,4,5,6-tetrahydro-1H-benz[de]isoquinolin-1-one, and to intermediates useful in such process.

8 Claims, No Drawings

PROCESS FOR PREPARING 2-(1-AZABICYCLO[2.2.2]OCT-3-YL)-2,3,3A,4,5,6-HEXAHYDRO-1H-BENZ[DE]ISOQUINOLIN-1-ONE

BACKGROUND OF THE INVENTION

1. Field of the Invention

This invention relates to a novel process for preparing 2-(1-azabicyclo[2.2.2]oct-3-yl)-2,3,3a,4,5,6-hexahydro-1H-benz[de]isoquinolin-1-one and the pharmaceutically acceptable salts thereof, which are 5-$HT_3$ receptor antagonists. This invention also relates to compounds which are intermediates useful for preparing 2-(1-azabicyclo[2.2.2]oct-3-yl)-2,3,3a,4,5,6-hexahydro-1H-benz[de]isoquinolin-1-one and pharmaceutically acceptable salts thereof.

2. Description of the Field 2-(1-Azabicyclo[2.2.2]oct-3-yl)-2,3,3a,4,5,6-hexahydro-1H-benz[de]isoquinolin-1-one and 2-(1-azabicyclo[2.2.2]oct-3-yl)-2,4,5,6-tetrahydro-1H-benz[de]isoquinolin-1-one and the pharmaceutically acceptable salts, individual stereoisomers and mixture of stereoisomers thereof are 5-$HT_3$ receptor antagonists. In addition, 2-(1-azabicyclo[2.2.2]oct-3-yl)-2,4,5,6-tetrahydro-1H-benz[de]isoquinolin-1-one and the salts, individual stereoisomers and mixture of stereoisomers thereof are useful in the preparation of 2-(1-azabicyclo[2.2.2]oct-3-yl)-2,3,3a,4,5,6-hexahydro-1H-benz[de]isoquinolin-1-one. Methods for using these 5-$HT_3$ antagonists and certain processes for their preparation, different from those described herein, are described in U.S. Pat. No. 5,202,333.

SUMMARY OF THE INVENTION

This invention relates to a process for preparing 2-(1-azabicyclo[2.2.2]oct-3-yl)-2,3,3a,4,5,6-hexahydro-1H-benz[de]isoquinolin-1-one and pharmaceutically acceptable salts, individual stereoisomers and mixtures of stereoisomers thereof, which process comprises (A) reacting a compound of Formula 5:

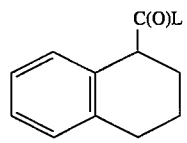

5 in which L is a leaving group, with 1-azabicyclo[2.2.2]oct-3-ylamine to give N-(1-azabicyclo[2.2.2]oct-3-yl)-1,2,3,4-tetrahydronaphthalen-1-ylcarboxamide;

(B) reducing the N-(1-azabicyclo[2.2.2]oct-3-yl)-1,2,3,4-tetrahydronaphthalen-1-ylcarboxamide to give (1-azabicyclo[2.2.2]oct-3-yl)-(1,2,3,4-tetrahydronaphthalen-1-ylmethyl)amine;

(C) reacting the (1-azabicyclo[2.2.2]oct-3-yl)(1,2,3,4-tetrahydronaphthalen-1-ylmethyl)amine with a formylating agent and then treating with a Lewis acid to give 2-(1-azabicyclo[2.2.2]oct-3-yl)-2,3,3a,4,5,6-hexahydro-1H-benz[de]isoquinolin-1-one;

(D) optionally separating a diastereomeric mixture of 2-(1-azabicyclo[2.2.2]oct-3-yl)-2,3,3a,4,5,6-hexahydro-1H-benz[de]isoquinolin-1-one into individual stereoisomers or mixtures of stereoisomers;

(E) optionally converting 2-(1-azabicyclo[2.2.2]oct-3-yl)-2,3,3a,4,5,6-hexahydro-1H-benz[de]isoquinolin-1-one to a pharmaceutically acceptable acid addition salt; and (F) optionally converting an acid addition salt of 2-(1-azabicyclo[2.2.2]oct-3-yl)-2,3,3a,4,5,6-hexahydro-1H-benz[de]isoquinolin-1-one to non-salt form.

A second aspect of the invention relates to a compound of Formula 6:

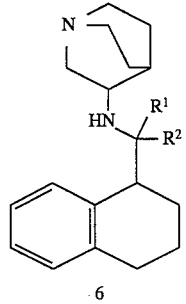

6 in which $R^1$ and $R^2$ are each hydrogen or together form =O; and the salts, individual stereoisomers and mixture of stereoisomers thereof.

DETAILED DESCRIPTION OF THE INVENTION

Definitions

As used herein:

"Leaving group" has the meaning conventionally associated with it in synthetic organic chemistry, i.e., an atom or group displaceable under alkylating conditions, and includes halo, ($C_{1-4}$)alkyloxy (e.g., methoxy, ethoxy and the like), aryloxy (e.g., phenyloxy and the like), $C_{1-4}$)alkylthio (e.g., methylthio, ethylthio and the like), arylthio (e.g., phenylthio and the like) and alkane- or arenesulfonyloxy (e.g., mesyloxy, ethanesulfonyloxy, benzenesulfonyloxy, trifluoromethanesufonyloxy, tosyloxy and the like).

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Acid addition salts" means salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

"Pharmaceutically acceptable acid addition salts" are salts which are pharmaceutically acceptable, as defined above, and which possess the desired pharmacological activity.

"Optional" or "optionally" means that the subsequently described event or circumstance may or may not occur, and that the description includes instances where the event or circumstance occurs and instances in which it does not. For example, "optionally converting the 2-(1-azabicyclo[2.2.2]oct-3-yl)-2,3,3a,4,5,6-hexahydro-1H-benz[de]isoquinolin- 1-one to a pharmaceutically acceptable acid addition salt" means that the conversion to the acid addition salt may or may not be carried out in order for the process described to fall within the invention, and the invention includes those processes wherein the conversion occurs and those processes in which it does not.

Isomerism is the phenomenon wherein compounds have identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes optical isomers. A carbon atom bonded to four nonidentical substituents is termed a "chiral center".

A compound with one chiral center has two enantiomeric forms of opposite chirality and may exist as either an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". For the purposes of this application, a mixture of stereoisomers containing one or more enantiomeric pairs is termed an "enantiomeric mixture" and a mixture of stereoisomers without their respective enantiomers present is termed a "non-enantiomeric mixture".

When one chiral center is present a stereoisomer may be characterized by the absolute configuration of that chiral center. Absolute configuration refers to the arrangement in space of the substituents attached to the chiral center. The substituents attached to the chiral center under consideration are ranked in accordance with the *Sequence Rule* of Cahn, Ingold and Prelog and the absolute descriptor R or S is cited in parentheses followed by a hyphen and the chemical name of compound (e.g., (S)-1-azabicyclo[2.2.2]oct-3-ylamine).

When a chiral center can be of either configuration individually or as a mixture thereof, in equal amounts or otherwise, no descriptor will appear. Accordingly, the compound of Formula 1 in which each of the chiral centers are in an S-configuration, that is, the compound of the following formula:

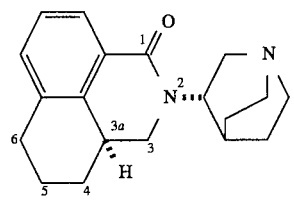

is referred to as 2-(1-azabicyclo[2.2.2]oct-3S-y1)-2,3,3aS,4,5,6-hexahydro-1H-benz[de]isoquinolin-1-one Preferred Embodiments While the broadest definition of this invention is set forth in the Summary of the Invention, compounds of Formula 6 and certain processes for the preparation of compounds of Formula 1 are preferred. For example, a preferred compound of Formula 6 is the S,S-stereoisomer thereof, namely N-(1-azabicyclo[2.2.2]oct-3S-yl)-1,2,3,4-tetrahydronaphthalen-1S-ylcarboxamide or (1-azabicyclo[2.2.2]oct-3S-yl)(1,2,3,4-tetrahydronaphthalen-1S-ylmethyl)-amine.

A preferred process for preparing 2-(1-azabicyclo[2.2.2]oct-3-yl)-2,3,3a,4,5,6-hexahydro-1H-benz[de]isoquinolin-1-one is that in which L is chloro and the 1-azabicyclo[2.2.2]oct-3-ylamine is (S)-1-azabicyclo[2.2.2]oct-3-ylamine and is reacted with the compound of Formula 5 to give N-(1-azabicyclo[2.2.2]oct-3S-yl)-1,2,3,4-tetrahydronaphthalen-1-ylcarboxamide; and preferably wherein the N-(1-azabicyclo[2.2.2]oct-3S-yl)-1,2,3,4-tetrahydronaphthalen-1-ylcarboxamide is then reduced as N-(1-azabicyclo[2.2.2]oct-3S-yl)-1,2,3,4-tetrahydronaphthalen-1S-ylcarboxamide.

Processes of the Invention:

The process of this invention is depicted in the following reaction scheme:

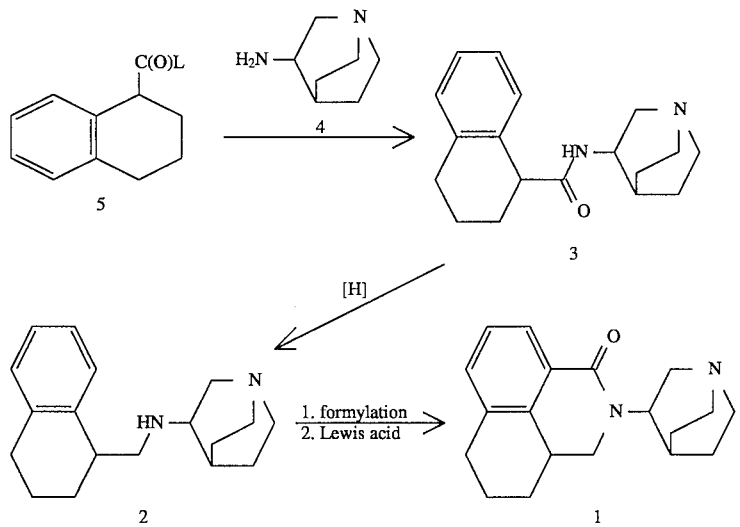

For the purposes of this application, when two or more chiral centers are present, the descriptor is cited immediately following the number of the chiral center as it appears in the name of the compound (e.g., 1-azabicyclo[2.2.2]oct-3S-yl).

in which L is a leaving group, Formulae 1, 2 and 3 represent an individual diastereomer or a diaetereomeric mixture, enantiomeric or otherwise, and Formulae 4 and 5 represent an individual enantiomer or an enantiomeric mixture, racemic or otherwise.

2-(1-Azabicyclo[2.2.2]oct-3-yl)-2,3,3a,4,5,6-hexahydro-1H-benz[de]isoquinolin-1-one (Formula 1) is prepared by reacting (1-azabicyclo[2.2.2]oct-3-yl)(1,2,3,4-tetrahydronaphthalen-1-ylmethyl)amine (Formula 2) with a suitable formylating agent (e.g., trichloromethyl chloroformate, 4-chlorophenyl chloroformate, 4-nitrophenyl chloroformate, triphosgene, phosgene, etc., preferably trichloromethyl chloroformate) and then treating with a suitable Lewis acid (e.g., boron trifluoride etherate, aluminum chloride, etc., preferably boron trifluoride etherate). The reaction with the chloroformate is carried out under a nitrogen atmosphere and in a suitable solvent, typically an aromatic hydrocarbon or ether and preferably an aromatic hydrocarbon (e.g., toluene, chlorobenzene, tetrahydrofuran (THF), etc., preferably toluene), at 50° to 132° C., typically at 95° to 125° C. and preferably at approximately 110° C., and requires 1 to 12 hours.

The treatment with the Lewis acid is carried out in a suitable solvent, typically an aromatic hydrocarbon (e.g., toluene, chlorobenzene, etc.) and preferably toluene, at 110° to 132° C., typically at 110° to 120° C. and preferably at approximately 110° C., and requires 4 to 18 hours. The preparation of a compound of Formula 1 is described in Example 6.

The compound of Formula 2 is prepared by reducing N-(1-azabicyclo[2.2.2]oct-3-yl)-1,2,3,4-tetrahydronaphthalen-1-ylcarboxamide (Formula 3). Reduction of the carboxamide is carried out with a chemical reducing agent, preferably borane, and in a suitable solvent, typically an ether and preferably THF, at reflux temperature, and requires 1 to 3 hours. The preparation of a compound of Formula 2 is described in Example 5.

The compound of Formula 3 is prepared by reacting a compound of Formula 5 with 1-azabicyclo[2.2.2]oct-3-ylamine (Formula 4). The reaction is carried out in a suitable solvent, typically a mixture of ester and aromatic hydrocarbon and preferably 4/1 to 3/1 ethyl acetate/toluene, at 25° to 50° C., typically at 40° to 50° C. and preferably at approximately 50° C., and requires 2 to 6 hours. The preparation of a compound of Formula 3 is described in Example 3.

1-Azabicyclo[2.2.2]oct-3-ylamine is commercially available or can be readily prepared by methods know to those of ordinary skill in the art. The compound of Formula 5 can be prepared by carboxylating 1,2,3,4-tetrahydronaphthalene to give 1,2,3,4-tetrahydro-1-naphthoic acid and then creating leaving group L. The carboxylation is carried out by treating the 1,2,3,4-tetrahydronaphthalene with strong base, preferably n-butyl potassium, and then reacting with carbon dioxide. The treatment with base and subsequent reaction with carbon dioxide is carried out in a suitable solvent, preferably hexane, at −78° to 20° C., typically at −50° to 20° C. and preferably at approximately 20° C., and requires 18 to 24 hours. The preparation of 1,2,3,4-tetrahydro-1-naphthoic acid is described in Example 1.

Creation of the leaving group L can be effected by treating the naphthoic acid with an agent such as methanesulfonyl chloride, thionylchloride, phosphorous pentachloride, phosphorous oxychloride, and the like. For example, a compound of Formula 5 in which L is chloro (i.e., 1,2,3,4-tetrahydro-1-naphthoic acid chloride) can be prepared by reacting 1,2,3,4-tetrahydro-1-naphthoic acid with thionylchloride in a suitable solvent, typically an aromatic hydrocarbon or halogenated hydrocarbon (e.g., toluene, methylene chloride, etc. preferably toluene), at 25° to 50° C., typically at 40° to 50° C. and preferably at approximately 50° C., and requires 1 to 2 hours.

Depending upon the reaction conditions, isolation/separation techniques and starting materials, the compounds of Formulae 1, 2, 3, 4 and 5 may be converted to or prepared as their non-salt or salt forms. The compounds of Formulae 1, 2, 3, 4 and 5 in the processes of this invention as its non-salt or acid addition salt form in order for the process described to fall within the invention, and the invention includes those processes wherein the compounds of Formulae 1, 2, 3, 4 and 5 are in non-salt form and those processes wherein the compounds are acid addition salts. Accordingly, while some forms of the compounds of Formulae 1, 2, 3, 4 and 5 are preferred, unless indicated otherwise, the description or naming of a particular compound in the specification or in the claims is intended to include both the non-salt form and salt forms, pharmaceutically acceptable or otherwise, thereof.

The compounds of Formulae 1, 2, 3, 4 and 5 each contain one or more chiral centers and can be separated into or prepared as individual stereoisomers and/or mixtures of stereoisomers. Accordingly, while some stereoisomers or mixtures of stereoisomers of the compounds of Formulae 1, 2, 3, 4 and 5 are preferred, unless indicated otherwise, the description or naming of a particular chiral compound in the specification or in the claims is intended to include individual stereoisomers and the mixtures, racemic or otherwise, thereof.

The individual stereoisomers of the compound of Formula 1 can be separated from a non-enantiomeric diastereomeric mixture of the compound of Formula 1 by chromatography, by separation/resolution techniques based upon differences in solubility, by direct or selective crystallization or by any other method known to one of ordinary skill in the art. For example, 2-(1-azabicyclo[2.2.2]oct-3S-yl)-2,3,3aS,4,5,6-hexahydro-1H-benz[de]isoquinolin-1-one hydrochloride is readily prepared from a diastereomeric mixture of 2-(1-azabicyclo[2.2.2]oct-3S-yl)-2,3,3a,4,5,6-hexahydro-1H-benz[de]isoquinolin-1-one hydrochloride by repeated crystallization from a suitable solvent, typically an alcohol and preferably isopropanol.

A non-enantiomeric diastereomeric mixture of the compound of Formula 1 can be prepared by reacting an enantiomeric diastereomeric mixture with an optically active acid (e.g., tartaric acid, mandelic acid, malic acid, the 2-arylpropionic acids in general, camphorsulfonic acid, etc.) to form diastereomeric crystalline salts. The non-enantiomeric diastereomeric mixture of crystalline salts are then separated into individual diastereomers by any of the methods described above and the pure diastereomers of the compound of Formula 1 are recovered, along with the optically active acid, by any practical means that would not result in racemization. A more detailed description of the techniques applicable to the preparation of stereoisomers can be found in Jean Jacques, Andre Collet, Samuel H. Wilen, Enantiomers, Racemates and Resolutions, John Wiley & Sons, Inc. (1981).

Alternatively, a non-enantiomeric diastereomeric mixture of the compound of Formula 1 can be prepared by proceeding as described above and reacting a non-enantiomeric diastereomeric mixture of a compound of Formula 2 with the formylating agent and then treating with a Lewis acid. A non-enantiomeric diastereomeric mixture of a compound of Formula 2 can be prepared by proceeding as described above and reducing a non-enantiomeric diastereomeric mixture of the compound of Formula 3. A non-enantiomeric diastereomeric mixture of the compound of Formula 3 can be prepared by proceeding as described above and reacting an individual enantiomer of the compound of Formula 4 with an enantiomeric mixture of the compound of Formula 5 or by reacting an individual enantiomer of the compound of Formula 5 with an enantiomeric mixture of the compound of Formula 4.

Similarly, the individual diastereomers of the compound of Formula 1 can be prepared by proceeding as described above and reacting an individual diastereomer of the compound of Formula 2 with the formylating agent and then treating with a Lewis acid. The individual diastereomers of the compound of Formula 2 can be prepared from a diastereomeric mixture of a compound of Formula 2 by any of the separation/resolution techniques described above or by proceeding as described above and reducing an individual diastereomer of the compound of Formula 3.

The individual diastereomers of the compound of Formula 3 can be prepared from a diastereomeric mixture of a compound of Formula 3 by any of the separation/resolution techniques described above. For example, N-(1-azabicyclo[2.2.2]oct-3S-yl)-1,2,3,4-tetrahydronaphthalen-1S-ylcarboxamide is readily prepared from N-(1-azabicyclo[2.2.2]oct-3S-yl)-1,2,3,4-tetrahydronaphthalen- 1-ylcarboxamide by repeated crystallization from a suitable solvent, typically a aromatic hydrocarbon and preferably toluene. The preparation of N-(1-azabicyclo[2.2.2]oct-3S-yl)-1,2,3,4-tetrahydronaphthalen-1S-ylcarboxamide is described in Example 4.

Alternatively, the individual diastereomers of the compound of Formula 3 can be prepared by proceeding as described above and reacting an individual enantiomer of the amine of Formula 4 with an individual enantiomer of the compound of Formula 5. The individual enantiomers of the compound of Formula 5 can be prepared from the corresponding enantiomer of 1,2,3,4-tetrahydro-1-naphthoic acid. The individual enantiomer of the naphthoic acid is conveniently prepared by reacting a enantiomeric mixture with a suitable optically active base. For example, the (S)-1,2,3,4-tetrahydro-1-naphthoic acid can be prepared by reacting an enantiomeric mixture of the acid with quinine in a suitable solvent (e.g., ethanol, acetone, etc. preferably ethanol), selectively crystallizing the quinine salt and then isolating the optically active acid. The preparation of (S)-1,2,3,4-tetrahydro-1-naphthoic acid is described in Example 2.

The individual enantiomers of the amine of Formula 4 can be separated from a enantiomeric mixture of the amine of Formula 4 by any of the applicable separation/resolution techniques described above. Alternatively, (S)-1-azabicyclo[2.2.2]oct-3-ylamine can be prepared by reacting 1-azabicyclo[2.2.2]oct-3-one with an (R)-α-alkylbenzylamine, preferably (R)-1-phenylethylamine, to give the corresponding (R)-N-(α-alkylbenzyl)-3-(1-azabicyclo[2.2.2]octan-)imine, reducing the imine to give the corresponding N-(1R-phenylalkyl)-1-azabicyclo[2.2.2]oct-3S-ylamine and then hydrogenolyzing. The reaction with the (R)-α-alkylbenzylamine is carried out in the presence of lithium oxide in a suitable organic solvent, typically an ether and preferably THF, at 10° to 40° C., typically at 15° to 30° C. and preferably at approximately 20° C., and requires 12 to 84 hours. The reduction of the imine can be carried out by catalytic hydrogenation or with a suitable chemical reducing agent.

Hydrogenation of the imine is carried out in the presence of a suitable catalyst, preferably 5% Pt/C, and in a suitable organic solvent, typically an alcohol and preferably ethanol, at 10° to 40° C., typically at 15 to 30° C. and preferably at approximately 20° C., and at 0 to 100 psig, typically at 5 to 50 psig and preferably at approximately 20 psig, and requires 1 to 48 hours. Alternatively, the imine can be reduced with a suitable chemical reducing agent, preferably an alkali borohydride (e.g., sodium borohydride, lithium borohydride, etc., preferably sodium borohydride), in a suitable organic solvent, typically an alcohol and preferably ethanol, at −15° to 50° C., typically at 15° to 30° C. and preferably at approximately 20° C., and requires 15 minutes to 3 hours.

The hydrogenolyzation is effected by hydrogenation the N-(1R-phenylalkyl)-1-azabicyclo[2.2.2]oct-3S-ylamine in the presence of a suitable catalyst (e.g., 10% Pd/C, 20% Pd/C, etc., preferably 10% Pd/C) and in a suitable organic solvent, typically an alcohol and water mixture and preferably 5/1 to 2/1 ethanol/water, at 10° to 40° C., typically at 15° to 30° C. and preferably at approximately 20° C., and at 0 to 100 psig, typically at 0 to 20 psig and preferably at approximately 5 psig, and requires 5 to 48 hours. Proceeding similarly but replacing the (R)-α-alkylbenzylamine with (S)-α-alkylbenzylamine, (R)-1-azabicyclo[2.2.2]oct-3-ylamine can be prepared.

Thus, the compounds of Formulae 1, 2, 3, 4 and 5 may exist as individual stereoisomers and/or any mixture of stereoisomers in order for the process described to fall within the invention, and the invention includes those processes wherein individual stereoisomers are used and those processes wherein mixtures of stereoisomers are used. An exemplary method of practicing the processes of this invention comprises (A) reacting 1,2,3,4-tetrahydro-1-naphthoic acid chloride with (S)-1-azabicyclo[2.2.2]oct-3-ylamine to give a diastereomeric mixture N-(1-azabicyclo[2.2.2]oct-3S-yl)-1,2,3,4-tetrahydronaphthalen-1-ylcarboxamide;

(B) separating the diastereomeric mixture of N-(1-azabicyclo[2.2.2]oct-3S-yl)-1,2,3,4-tetrahydronaphthalen-1-ylcarboxamide into individual diastereomers and reducing N-(1-azabicyclo[2.2.2]oct-3S-yl)-1,2,3,4-tetrahydronaphthalen-1S-ylcarboxamide to give (1-azabicyclo[2.2.2]oct-3S-yl)-(1,2,3,4-tetrahydronaphthalen-1S-ylmethyl)amine;

(C) reacting the (1-azabicyclo[2.2.2]oct-3S-yl)(1,2,3,4-tetrahydronaphthalen- 1S-ylmethyl)amine with a formylating agent and then treating with a Lewis acid to give 2-(1-azabicyclo[2.2.2]oct-3S-yl)-2,3,3aS,4,5,6-hexahydro-1H-benz[de]isoquinolin-1-one; and (D) converting the 2-(1-azabicyclo[2.2.2]oct-3S-yl)-2,3,3aS,4,5,6-hexahydro-1H-benz[de]isoquinolin-1-one to a pharmaceutically acceptable acid addition salt.

While the process steps described immediately above represent one particular method of practicing the processes of the invention, it should be understood that other variations in the process steps can occur without deviating from the scope of the invention. For example, (S)-1,2,3,4-tetrahydro-1-naphthoic acid can be reacted with (S)-1-azabicyclo[2.2.2]oct-3-ylamine to give N-(1-azabicyclo[2.2.2]oct-3S-yl)-1,2,3,4-tetrahydronaphthalen-1S-ylcarboxamide which is reduced to give (1-azabicyclo[2.2.2]oct-3S-yl)(1,2,3,4-tetrahydronaphthalen-1S-ylmethyl)amine.

EXAMPLE 1

1,2,3,4-Tetrahydro-1-naphthoic Acid

A mixture of potassium tert-butoxide (74.13 g, 661 mmol) and N,N,N',N'-tetramethylethylenediamine (6.63M, 78.92 mL, 523 mmol) in 1.7 L of hexane was cooled to below −30° C. under a nitrogen atmosphere and then n-butyl lithium (1.6M, 327 mL, 523 mmol) was added over 15 minutes. The mixture was stirred for 15 minutes and 1,2,3,4-tetrahydronapthalene (7.36M, 85.27 mL, 623 mmol) was added. The mixture was stirred for 6 hours at 0° C. and then for 18 hours at between 0° and 20° C. The mixture was aerated with carbon dioxide for approximately 30 minutes and then approximately 1.2 L of water was added. The aqueous layer was separated, cooled in an ice-water bath and acidified with approximately 185 mL of 12N hydrochloric acid. The mixture was then extracted with ethyl acetate (2×1 L) and the combined ethyl acetate layers were dried (NaSO$_4$). The mixture was filtered and concentrated. The residue was dissolved in 170 mL of formic acid and then the solution was diluted with 340 mL of water to give a crystalline product. The product was isolated by filtration, washed with 40 mL of water and dried. The dry material was dissolved in 0.74 L of ethyl acetate and the solution was washed with 0.5 L of water, dried (Na$_2$SO$_4$) and concentrated to give 1,2,3,4-tetrahydro-1-naphthoic acid (38.68 g, 219.6 mol), m.p. 74.4°–79.2° C.

EXAMPLE 2

(S)-1,2,3,4-Tetrahydro-1-naphthoic Acid

A solution of 1,2,3,4-tetrahydro-1-naphthoic acid (50.66 g, 290 mmol) and quinine (93.67 g, 290 mmol) in 937 mL of ethanol and 150 mL of water was cooled to approximately 0° C., seeded with crystals of (S)-1,2,3,4-tetrahydro-1-naphthoic acid and allowed to stand for approximately 24 hours to give a precipitate. The precipitate was isolated by filtration and dried. The dry crystals were crystallized from 540 mL of ethanol, filtered and dried to give quinine salt (46.18 g, 92 mmol).

The quinine salt was suspended in 180 mL of ethyl acetate and the suspension was washed with 1N hydrochloric acid (2×92 mL). The mixture was then dried (NaSO$_4$), filtered and concentrated. The residue was dissolved in hexane and crystallized to give (S)-1,2,3,4-tetrahydro-1-naphthoic acid (14.27 g 0.08 mol), m.p. 54°–56° C. [α]$_D$ –62.76° (c=1.0165, benzene).

EXAMPLE 3

N-(1- Azabicyclo[2.2.2]oct-3S-yl)-1,2,3,4 -tetrahydronaphthalen-1-ylcarboxamide

A mixture of 1,2,3,4-tetrahydro-1-naphthoic acid (207.75 g, 1.18 mol), prepared as in Example 1, and thionyl chloride (13.7M, 92.89 mL, 1.27 mol) in 20 drops of N,N-dimethylformamide and 795 mL of toluene was stirred for 1 hour at 25° C. and for 1 hour at 50° C. The mixture was distilled to a volume of approximately 500 mL and then diluted with 300 mL of toluene.

(S)-1-Azabicyclo[2.2.2]oct-3-ylamine (148.83 g, 1.16 mol) in 2.895 L of ethyl acetate was added and the mixture was stirred for 1 hour at 50° C. The mixture was allowed to cool to room temperature and 2 L of water and 93.4 mL of 50% sodium hydroxide were added. The aqueous layer was separated and extracted with ethyl acetate (2×1.5 L). The combined ethyl acetate layers were dried (NaSO$_4$), filtered and concentrated to give N-(1-azabicyclo[2.2.2]oct-3S-yl)-1,2,3,4-tetrahydronaphthalen-1-ylcarboxamide (350.3 g, 1.23 mol), m.p. 190.1°–191.2° C.

Proceeding as in Example 3, but replacing 1,2,3,4-tetrahydro-1-naphthoic acid with (S)-1,2,3,4-tetrahydro-1-naphthoic acid, prepared as in Example 2, gave N-(1-azabicyclo[2.2.2]oct-3S-yl)-1,2,3,4-tetrahydronaphthalen-1S-ylcarboxamide, m.p. 190°–191° C. [α]$_D$ –51.26° (C=1.0145, methylene chloride).

EXAMPLE 4

N-(1-Azabicyclo[2.2.2]oct-3S-yl)- 1,2,3,4-tetrahydronaphthalen-1S-ylcarboxamide

N-(1-Azabicyclo[2.2.2]oct-3S-yl)-1,2,3,4-tetrahydronaphthalen-1-yl-carboxamide (350.3 g, 1.23 mol), prepared as in Example 3, was dissolved in 1.4 L of boiling toluene and the solution was cooled to give a crystalline precipitate. The precipitate was isolated by filtration and dried to give a diastereomeric mixture of 82% N-(1-azabicyclo[2.2.2]oct-3S-yl)-1,2,3,4-tetrahydronaphthalen-1S-ylcarboxamide (A) and 18% N-(1-azabicyclo[2.2.2]oct-3S-yl)-1,2,3,4-tetrahydronaphthalen-1R-ylcarboxamide (B) (128.63 g, 0.45 mol).

The 82% A/18% B mixture was dissolved in 514 mL of boiling toluene and the solution was cooled to give a crystalline precipitate. The precipitate was isolated by filtration and dried to give 92.5% pure N-(1-azabicyclo[2.2.2]oct-3S-yl)-1,2,3,4-tetrahydronaphthalen-1S-ylcarboxamide (110.17 g, 0.39 mol), m.p. 190°–191° C. [α]$_D$ –26.24° (c=2.004, methylene chloride).

EXAMPLE 5

(1-Azabicyclo[2.2.2]oct-3S-yl)(1,2,3,4-tetrahydronaphthalen-1S-ylmethyl)amine

A mixture of N-(1-azabicyclo[2.2.2]oct-3S-yl)-1,2,3,4-tetrahydronaphthalen- 1S-ylcarboxamide (85 g, 0.3 mol), prepared as in Example 3 or 4, and sodium borohydride (45.22 g) in 1.7 L of THF was cooled to below 15° C. Boron trifluoride etherate (8.1M, 195.92 mL, 1.59 mol) was added over 20 minutes and the mixture was stirred for 30 minutes at room temperature and then at reflux for 2 hours. The mixture was cooled to below 20° C. and 1.222 L of 2N hydrochloric acid was added slowly. The mixture was distilled to a volume of approximately 1.4 L. The remaining mixture was cooled and 50% potassium hydroxide (512 g) was added. The mixture was extracted with ethyl acetate (1×1.2 L and 2×500 mL). The combined ethyl acetate layers were dried (NaSO$_4$), filtered and concentrated to give (1-azabicyclo[2.2.2]oct-3S-yl)-(1,2,3,4-tetrahydronaphthalen-1S-ylmethyl)amine (80.96 g, 0.3 mol) as an oil. [α]$_D$ –32.01° (c=1.0185, methylene chloride).

EXAMPLE 6

2-(1-Azabicyclo[2.2.2]oct-3S-yl)-2,3,3aS,4,5,6-hexahydro-1H-benz[de]isoquinolin-1-one hydrochloride A solution of (1-azabicyclo[2.2.2]oct-3S-yl)(1,2,3,4-tetrahydronaphthalen- 1S-ylmethyl)amine (80.15 g, 0.3 mol), prepared as in Example 5, in 0.81 L of toluene was heated to reflux under a nitrogen atmosphere and then cooled to 25° C. Trichloromethyl chloroformate (8.3M, 25.28 mL, 0.21 mmol) in 100 mL of toluene was added at a rate such that the temperature of the mixture remained below 50° C. The mixture was stirred for approximately 18 hours and then boron trifluoride etherate (8.1M, 110.28 mL, 0.893 mol) was added. The mixture was heated at reflux for 5 hours, cooled to 30° C. and then 455 mL of 2N hydrochloric acid and 455 mL of water were added. The mixture was heated at reflux for 1 hour, cooled to 10° C. and then 50% potassium hydroxide (200 g) was added at a rate such that the temperature of the mixture remained below 40° C. The mixture was added to 0.8 L of ethyl acetate and filtered. The aqueous layer was separated and extracted with ethyl acetate (2×0.6

L). The combined ethyl acetate layers were concentrated and the residue was dissolved in 1.08 L of isopropanol. The solution was treated with 82 m L of 4N hydrogen chloride in ethanol and cooled to below 5° C. to give a crystalline precipitate. The precipitate was isolated by filtration and dried to give 75.06 g of solid material.

The solid material was dissolved in 1.2 L of isopropanol and 60 mL of water at reflux temperature and then 500 mL of additional isopropanol was added. The mixture was distilled to a volume of approximately 1.2 L and then allowed to cool to room temperature. The mixture was cooled in an ice-water bath for 2 hours to give a crystalline product. The product was isolated by filtration to give 2-(1-azabicyclo[2.2.2]oct-3S-yl)-2,3,3aS,4,5,6-hexahydro-1H-benz[de]isoquinolin-1-one hydrochloride (64.41 g, 0.19 mol), m.p. 303° C. (dec). $[\alpha]_D$ 90° (C=1, chloroform).

We claim:

1. A process for preparing 2-(1-azabicyclo[2.2.2]oct-3-yl)-2,3,3a,4,5,6-hexahydro-1H-benz[de]isoquinolin-1-one and the pharmaceutically acceptable salts, individual stereoisomers and mixture of stereoisomers thereof, which process comprises:

(A) reacting a compound of Formula 5:

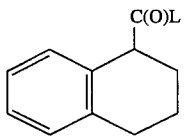

in which L is a leaving group, with 1-azabicyclo[2.2.2]oct-3-ylamine to give N-(1-azabicyclo[2.2.2]oct-3-yl)-1,2,3,4-tetrahydronaphthalen-1-ylcarboxamide;

(B) reducing the N-(1-azabicyclo[2.2.2]oct-3-yl)-1,2,3,4-tetrahydronaphthalen- 1-ylcarboxamide to give (1-azabicyclo[2.2.2]oct-3-yl)-(1,2,3,4-tetrahydronaphthalen-1-ylmethyl)amine;

(C) reacting the (1-azabicyclo[2.2.2]oct-3-yl)(1,2,3,4-tetrahydronaphthalen- 1-ylmethyl)amine with a formylating agent and then treating with a Lewis acid to give 2-(1-azabicyclo[2.2.2]oct-3-yl)-2,3,3a,4,5,6-hexahydro-1H-benz[de]isoquinolin-1-one; and (D) optionally separating a diastereomeric mixture of the 2H-(1-azabicyclo[2.2.2]oct-3-yl)-2,3,3a,4,5,6-hexahydro-1H-benz[de]isoquinolin-1-one into individual stereoisomers or mixtures of stereoisomers;

(E) optionally converting the 2-(1-azabicyclo[2.2.2]oct-3-yl)-2,3,3a,4,5,6-hexahydro-1H-benz[de]isoquinolin-1-one to a pharmaceutically acceptable acid addition salt; and (F) optionally converting an acid addition salt of the 2-(1-azabicyclo[2.2.2]oct-3-yl)-2,3,3a,4,5,6-hexahydro-1H-benz[de]isoquinolin-1-one to non-salt form.

2. The process of claim 1 in which L is chloro and the 1-azabicyclo[2.2.2]oct-3-ylamine is (S)-1-azabicyclo[2.2.2]oct-3-ylamine and is reacted with the compound of Formula 5 to give N-(1-azabicyclo[2.2.2]oct-3S-yl)-1,2,3,4-tetrahydronaphthalen-1-ylcarboxamide.

3. The process of claim 2 in which the N-(1-azabicyclo[2.2.2]oct-3S-yl)-1,2,3,4-tetrahydronaphthalen-1-ylcarboxamide is N-(1-azabicyclo[2.2.2]oct-3S-yl)-1,2,3,4-tetrahydronaphthalen-1S-ylcarboxamide.

4. A process for preparing 2-(1-azabicyclo[2.2.2]oct-3-yl)-2,3,3a,4,5,6-hexahydro-1H-benz[de]isoquinolin-1-one and the pharmaceutically acceptable salts, individual stereoisomers and mixture of stereoisomers thereof, which process comprises:

(A) reducing N-(1-azabicyclo[2.2.2]oct-3-yl)-1,2,3,4-tetrahydronaphthalen- 1-ylcarboxamide to give (1-azabicyclo[2.2.2]oct-3-yl)-(1,2,3,4-tetrahydronaphthalen-1-ylmethyl)amine;

(B) reacting the (1-azabicyclo[2.2.2]oct-3-yl)(1,2,3,4-tetrahydronaphthalen- 1-ylmethyl)amine with a formylating agent and then treating with a Lewis acid to give 2-(1-azabicyclo[2.2.2]oct-3-yl)-2,3,3a,4,5,6-hexahydro-1H-benz[de]isoquinolin-1-one; and (C) optionally separating a diastereomeric mixture of the 2-(1-azabicyclo[2.2.2]oct-3-yl)-2,3,3a,4,5,6-hexahydro-1H-benz[de]isoquinolin-1-one into individual stereoisomers or mixtures of stereoisomers;

(D) optionally converting the 2-(1-azabicyclo[2.2.2]oct-3-yl)-2,3,3a,4,5,6-hexahydro-1H-benz[de]isoquinolin-1-one to a pharmaceutically acceptable acid addition salt; and (E) optionally converting an acid addition salt of the 2-(1-azabicyclo[2.2.2]oct-3-yl)-2,3,3a,4,5,6-hexahydro-1H-benz[de]isoquinolin-1-one to non-salt form.

5. The process of claim 4 in which the N-(1-azabicyclo[2.2.2]oct-3-yl)-1,2,3,4-tetrahydronaphthalen-1-ylcarboxamide is N-(1-azabicyclo[2.2.2]oct-3S-yl)-1,2,3,4-tetrahydronaphthalen-1-ylcarboxamide.

6. The process of claim 5 in which the N-(1-azabicyclo[2.2.2]oct-3S-yl)-1,2,3,4-tetrahydronaphthalen-1-ylcarboxamide is N-(1-azabicyclo[2.2.2]oct-3S-yl)-1,2,3,4-tetrahydronaphthalen-1S-ylcarboxamide.

7. A process for preparing 2-(1-azabicyclo[2.2.2]oct-3-yl)-2,3,3a,4,5,6-hexahydro-1H-benz[de]isoquinolin-1-one and the pharmaceutically acceptable salts, individual stereoisomers and mixture of stereoisomers thereof, which process comprises:

(A) reacting (1-azabicyclo[2.2.2]oct-3-yl)(1,2,3,4-tetrahydronaphthalen- 1-ylmethyl)amine with a formylating agent and then treating with a Lewis acid to give 2-(1-azabicyclo[2.2.2]oct-3-yl)-2,3,3a,4,5,6-hexahydro-1H-benz[de]isoquinolin-1-one; and (B) optionally separating a diastereomeric mixture of the 2-(1-azabicyclo[2.2.2]oct-3-yl)-2,3,3a,4,5,6-hexahydro-1H-benz[de]isoquinolin-1-one into individual stereoisomers or mixtures of stereoisomers;

(C) optionally converting the 2-(1-azabicyclo[2.2.2]oct-3-yl)-2,3,3a,4,5,6-hexahydro-1H-benz[de]isoquinolin-1-one to a pharmaceutically acceptable acid addition salt; and (D) optionally converting an acid addition salt of the 2-(1-azabicyclo[2.2.2]oct-3-yl)-2,3,3a,4,5,6-hexahydro-1H-benz[de]isoquinolin-1-one to non-salt form.

8. The process of claim 7 in which the (1-azabicyclo[2.2.2]oct-3-yl)(1,2,3,4-tetrahydronaphthalen-1-ylmethyl)amine is (1-azabicyclo[2.2.2]oct-3S-yl)(1,2,3,4-tetrahydronaphthalen-1S-ylmethyl)amine.

* * * * *